(12) United States Patent
Lee et al.

(10) Patent No.: US 7,955,259 B2
(45) Date of Patent: Jun. 7, 2011

(54) APPARATUS AND METHOD FOR INDUCING EMOTIONS

(75) Inventors: Mihee Lee, Kyungki-do (KR); Seokwon Bang, Seoul (KR); Gyunghye Yang, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1478 days.

(21) Appl. No.: 10/603,787

(22) Filed: Jun. 26, 2003

(65) Prior Publication Data

US 2005/0075532 A1     Apr. 7, 2005

(30) Foreign Application Priority Data

Jun. 26, 2002  (KR) .................. 10-2002-0035953

(51) Int. Cl.
*A61G 10/00* (2006.01)
(52) U.S. Cl. .................. 600/301; 600/27; 128/905
(58) Field of Classification Search .......... 600/300–301; 128/903–905; 434/236–238
See application file for complete search history.

(56) References Cited

U.S. PATENT DOCUMENTS

| | | | |
|---|---|---|---|
| 4,195,626 A | | 4/1980 | Schweizer |
| 4,909,260 A | * | 3/1990 | Salem et al. .................. 600/484 |
| 5,219,322 A | | 6/1993 | Weathers |
| 5,266,070 A | * | 11/1993 | Hagiwara et al. .............. 600/27 |
| 5,725,472 A | | 3/1998 | Weathers |

FOREIGN PATENT DOCUMENTS

| | | |
|---|---|---|
| EP | 0872255 A1 | 10/1998 |
| JP | 8-117300 | 5/1996 |
| JP | 8-299462 | 11/1996 |
| JP | 10-076012 A | 3/1998 |
| JP | 2000-005317 A | 1/2000 |
| JP | 2002-112969 A | 4/2002 |
| KR | 2002-0018541 | 3/2002 |
| WO | WO01/06921 A1 | 2/2001 |

OTHER PUBLICATIONS

Office Action Issued by the Japanese Patent Office on May 17, 2006.
European Search report dated Oct. 3, 2003 in corresponding application EP 03 25 3963.

* cited by examiner

*Primary Examiner* — Henry M Johnson, III
*Assistant Examiner* — Bobby Soriano
(74) *Attorney, Agent, or Firm* — Staas & Halsey LLP

(57) ABSTRACT

The present invention relates to an apparatus and method for inducing emotions. A primary object of the present invention is to accurately induce an emotion desired by a user by feedbacking biosignals from the user and inducing a desired emotion in accordance with the feedback biosignals. The object of the invention can be achieved by allowing the user to select the desired emotion, outputting physical signals for stimulating the user's body based on an emotion induction protocol capable of inducing the selected emotion, extracting bioparameters from the biosignals detected from the user's body before and after the output of the physical signals for stimulating the user's body, comparing increase/decrease patterns of the extracted respective bioparameters with increase/decrease patterns of bioparameter change models for the emotional state desired by the user, and controlling the emotion induction protocol based on comparative results.

34 Claims, 12 Drawing Sheets

Fig. 5

| E | Pleasure | Sadness | Anger | Fear | Disgust | Surprise |
|---|---|---|---|---|---|---|
| Illumination | Orange Yellow Red having high chroma Vivid red | Blue Amber Indigo Gray Black | Red having high chroma | Cyan White Black Blue having low chroma | Red Magenta | Combination of complementary colors |
| Fragrance | Lilac, Rose, Grapefruit, Jasmine, Lavender, Melisa, Neroli, Palmarosa, Ylang-ylang, Ginger, Lemon, Pachouli, Teatree, Camomile | Bergamot, Orange, Camomile roman, Grapefruit, Lavender, Melisa, Neroli, Peppermint | Jasmine, Peppermint, Juniper, Bergamot, Rosemary, Frankincense, Cypress, Sandalwood, Geranium | Peppermint, Basil, Neroli, Bergamot, Lavender, Sandalwood, Geranium, Hyssop, Clarysage | Peppermint, Basil, Neroli, Bergamot, Lavender, Sandalwood, Geranium, Hyssop, Clarysage | Juniper, Rosemary, Frankincense |
| Contents | Cheer, Victory, Pregnancy, Wedding ceremony | Koryo burial practice, Death of parents, Parting | Massacre, Rape, Cruelty | Pursued, Strain, Gloomy atmosphere | Cut corpse, Disgusting animal, Blood mess | Accident, Sound effects |

Fig. 6a

Pleasure

| Level | 0 |
|---|---|
| Illumination | Yellowish Red |
| Fragrance | Grapefruit |
| Temperature/Humidity | 26℃/70% |
| Contents | Wedding Ceremony |

HR

| Level | -3 | -2 | -1 | 1 | 2 | 3 |
|---|---|---|---|---|---|---|
| Illumination | Cyan | Blue | Gray | Yellow | Orange | Red |
| Fragrance | Sandalwood +Ylang-ylang | Ylang-ylang +Palmarosa | Palmarosa | Lavender | Lemon +Lavender | Lemon +Lavender |

SCRM

| Level | -3 | -2 | -1 | 1 | 2 | 3 |
|---|---|---|---|---|---|---|
| Illumination | Cyan | Yellow | Blue | Pink | Orange | Red |
| Fragrance | Cypress | Bergamot | Rose | Jasmine | Jasmine +Lavender | Ylang-ylang |
| Temperature/Humidity | -3℃/15% | -2℃/10% | -1℃/5% | +1℃/5% | +2℃/10% | +3℃/15% |

HRV

| Level | -3 | -2 | -1 | 1 | 2 | 3 |
|---|---|---|---|---|---|---|
| Illumination | Green | Cyan | Blue | Red | Yellow-based red | Pink |
| Fragrance | Valeric acid | Cypress +Jasmine | Cypress | Lavender | Orange +Lavender | Ylang-ylang +Lavender |

Fig. 6b

Sadness

| Level | 0 |
|---|---|
| Illumination | Cyan |
| Fragrance | Bergamot |
| Temperature/Humidity | 26℃/70% |
| Contents | Parting |

HR

| Level | -3 | -2 | -1 | 1 | 2 | 3 |
|---|---|---|---|---|---|---|
| Illumination | Cyan | Blue | Gray | Yellow | Orange | Red |
| Fragrance | Geranium | Cypress | Bergamot | Rose | Rose +Jasmine | Juniper +Bergamot |

SCRM

| Level | -3 | -2 | -1 | 1 | 2 | 3 |
|---|---|---|---|---|---|---|
| Illumination | Cyan | Amber | Blue | Pink | Orange | Red |
| Fragrance | Palmarosa +Ylang-ylang | Palmarosa +Bergamot | Rose | Bergamot | Bergamot +Lavender | Bergamot +Cypress |
| Temperature/Humidity | -3℃/15% | -2℃/10% | -1℃/5% | +1℃/5% | +2℃/10% | +3℃/15% |

HRV

| Level | -3 | -2 | -1 | 1 | 2 | 3 |
|---|---|---|---|---|---|---|
| Illumination | | | | | | |
| Fragrance | | | | | | |

Fig. 6c

Anger

| Level | 0 |
|---|---|
| Illumination | Red |
| Fragrance | Peppermint |
| Temperature/Humidity | 26℃/70% |
| Contents | Rape |

HR

| Level | -3 | -2 | -1 | 1 | 2 | 3 |
|---|---|---|---|---|---|---|
| Illumination | White | Blue | Gray | Yellow-based red | Orange | Red |
| Fragrance | Sandalwood +Ylang-ylang | Cypress +Sandalwood | Cypress | Pheromone | Juniper | Juniper |

SCRM

| Level | -3 | -2 | -1 | 1 | 2 | 3 |
|---|---|---|---|---|---|---|
| Illumination | Cyan | Yellow | Yellowish green | Pink | Black | Red |
| Fragrance | Cypress +Geranium | Cypress | Jasmine | Juniper | Juniper | Juniper |
| Temperature/Humidity | -3℃/15% | -2℃/10% | -1℃/5% | +1℃/5% | +2℃/10% | +3℃/15% |

HRV

| Level | -3 | -2 | -1 | 1 | 2 | 3 |
|---|---|---|---|---|---|---|
| Illumination | Green | Yellowish green | Blue | Red | Violet | Pink |
| Fragrance | Jasmine +Cypress | Cypress | Rose | Ylang-ylang | Lavender +Ylang-ylang | Lemon +Ylang-ylang |

Fig. 6d ( Fear )

| Level | 0 |
|---|---|
| Illumination | White |
| Fragrance | Peppermint |
| Temperature/Humidity | 26℃/70% |
| Contents | Gloomy place |

HR

| Level | -3 | -2 | -1 | 1 | 2 | 3 |
|---|---|---|---|---|---|---|
| Illumination | Cyan | Blue | Gray | Red | Blue-based green | Black |
| Fragrance | Sandalwood +Ylang-ylang | Cypress +Sandalwood | Cypress | Caraway | Juniper | Juniper |

SCRM

| Level | -3 | -2 | -1 | 1 | 2 | 3 |
|---|---|---|---|---|---|---|
| Illumination | Cyan | Yellow | Blue | Blue-based green | Black | Red |
| Fragrance | Lemon +Ylang-ylang | Ylang-ylang | Ylang-ylang +Jasmine | Juniper | Juniper | Juniper |
| Temperature/Humidity | -3℃/15% | -2℃/10% | -1℃/5% | +1℃/5% | +2℃/10% | +3℃/15% |

HRV

| Level | -3 | -2 | -1 | 1 | 2 | 3 |
|---|---|---|---|---|---|---|
| Illumination | Green | Cyan | Blue | Red | Magenta | Blue-based green |
| Fragrance | Geranium +Sandalwood | Rose +Sandalwood | Ylang-ylang | Clinical reagent | Peppermint | |

Fig. 6e ( Disgust )

| Level | 0 |
|---|---|
| Illumination | Magenta |
| Fragrance | Peppermint |
| Temperature/Humidity | 26℃/70% |
| Contents | Cut corpse |

HR

| Level | -3 | -2 | -1 | 1 | 2 | 3 |
|---|---|---|---|---|---|---|
| Illumination | Cyan | Blue | Gray | Yellow | Orange | Red |
| Fragrance | Sandalwood +Ylang-ylang | Cypress +Sandalwood | Cypress | Pheromone | Juniper | Juniper |

SCRM

| Level | -3 | -2 | -1 | 1 | 2 | 3 |
|---|---|---|---|---|---|---|
| Illumination | Cyan | Gray | Blue | Pink | Yellow | Red |
| Fragrance | Lemon +Ylang-ylang | Lavender +Ylang-ylang | Apple | Juniper | Juniper | Juniper |
| Temperature/Humidity | -3℃/15% | -2℃/10% | -1℃/5% | +1℃/5% | +2℃/10% | +3℃/15% |

HRV

| Level | -3 | -2 | -1 | 1 | 2 | 3 |
|---|---|---|---|---|---|---|
| Illumination | Green | Cyan | Blue | Red | Violet | Pink |
| Fragrance | Geranium +Sandalwood | Rose +Sandalwood | Ylang-ylang | Clinical reagent | Peppermint | |

Fig. 6f

Surprise

| Level | 0 |
|---|---|
| Illumination | Contrast of complementary colors |
| Fragrance | Rosemary |
| Temperature/Humidity | 26℃/70% |
| Contents | Accident |

HR

| Level | -3 | -2 | -1 | 1 | 2 | 3 |
|---|---|---|---|---|---|---|
| Illumination | Cyan | Blue | Gray | Yellow | Orange | Red |
| Fragrance | Palmarosa +Ylang-ylang | Ylang-ylang | Palmarosa | Juniper | Juniper | Juniper |

SCRM

| Level | -3 | -2 | -1 | 1 | 2 | 3 |
|---|---|---|---|---|---|---|
| Illumination | Cyan | Blue-based green | Blue | Pink | Black | Red |
| Fragrance | Lemon | Mulberry | Lavender | Juniper | Privet | |
| Temperature/Humidity | -3℃/15% | -2℃/10% | -1℃/5% | +1℃/5% | +2℃/10% | +3℃/15% |

HRV

| Level | -3 | -2 | -1 | 1 | 2 | 3 |
|---|---|---|---|---|---|---|
| Illumination | Gray | Cyan | Blue | Red | Yellow | Pink |
| Fragrance | Bergamot +Cypress | Bergamot | Cypress | Juniper | Juniper | Juniper |

Fig. 7

| Total | HR | SCRM | HRV |
|---|---|---|---|
| Pleasure | ⇩ | ⬆ | ⇧ |
| Sadness | ⇩ | ⇧ | — |
| Anger | ⬆ | ⬆ | ⇩ |
| Fear | ⇩ | ⬆ | ⇧ |
| Disgust | ⬇ | ⇧ | ⇧ |
| Surprise | ⬇ | ⬆ | ⬆ |

| Bioparameter change model | — | — | — | ⇑ | ⇑ | ⇑ | ⇓ | ⇓ | ⇓ |
|---|---|---|---|---|---|---|---|---|---|
| Increase/decease pattern of bioparameter | — | ⇑ | ⇓ | — | ⇑ | ⇓ | — | ⇑ | ⇓ |
| Deviation $d_0$ | 0 | -1 | 1 | 1 | 0 | 1 | -1 | -1 | 0 |

<SCRM>

| Bioparameter change model | — | — | — | ⇑ | ⇑ | ⇑ | ⇓ | ⇓ | ⇓ |
|---|---|---|---|---|---|---|---|---|---|
| Increase/decease pattern of bioparameter | — | ⇑ | ⇓ | — | ⇑ | ⇓ | — | ⇑ | ⇓ |
| Deviation $d_1$ | 0 | -1 | 1 | 1 | 0 | 1 | -1 | -1 | 0 |

<HRV>

| Bioparameter change model | — | — | — | ⇑ | ⇑ | ⇑ | ⇓ | ⇓ | ⇓ |
|---|---|---|---|---|---|---|---|---|---|
| Increase/decease pattern of bioparameter | — | ⇑ | ⇓ | — | ⇑ | ⇓ | — | ⇑ | ⇓ |
| Deviation $d_2$ | 0 | -1 | 1 | 1 | 0 | 1 | -1 | -1 | 0 |

Fig. 9

|  | Pleasure | Sadness | Anger | Fear | Disgust | Surprise |
|---|---|---|---|---|---|---|
| First ranking | SCRM | HR | SCRM | SCRM | HR | HRV |
| Second ranking | HRV | SCRM | HR | HR | HRV | SCRM |
| Third ranking | HR | HRV | HRV | HRV | SCRM | HRV |

APPARATUS AND METHOD FOR INDUCING EMOTIONS

BACKGROUND OF THE INVENTION

1. Field of the Invention

The present invention relates to an apparatus and method for inducing emotions, and more particularly, to an apparatus and method for inducing emotions, wherein biosignals from a user are fedback and thus an emotion desired by a user can be accurately induced in accordance with the fedback biosignals.

2. Description of the Prior Art

An emotion generally means a mental state that is expressed as a change in feelings and a change in physiological activation due to an internal or external stimulus. As to the various emotions, there are positive emotions such as love, ecstasy, satisfaction, or kindliness, and negative emotions such as sadness, anger, fear, or disgust.

There have been proposed various models for emotion induction according to methods of analyzing an emotion and relationships between the emotion and the autonomic nervous system in view of psychology. First, there is the James-Lange Theory that an emotion is induced by cognizing a physiological change. Second, there is the Cannon-Bard Theory that emotion determination is first made by the central nervous system and then a response of the autonomic nervous system occurs.

The emotion induction theories will be described in more detail. The James-Lange Theory states that a bodily change does not occur due to the emotion, but it first occurs in a certain situation and then a particular emotion is induced upon cognition of such bodily change. That is, it is asserted that tears are not shed due to sadness, but the sadness is felt since the tears are shed. On the contrary, the Cannon-Bard Theory states that after the central nervous system cognizes the emotion in response to the internal or external stimulus and a physiological response of the autonomic nervous system is then induced.

In recent, emotion induction methods for attempting prevention and treatment of various diseases, skin care, metabolism adjustment and psychological stability are widely performed in various fields by inducing positive emotions in a user using music, fragrance, images or the like based on such emotion induction theories.

As an example of such emotion induction methods, U.S. Pat. No. 5,219,322 discloses a psychotheraphy apparatus wherein a patient's range of lateral eye movement and physiological responses are monitored and visual and auditory stimuli are controllably presented to the patient so as to elicit and eliminate a mental imagery of a negative experience of the patient and to substitute a positive experience reinforcing a desired new behavior, as shown in FIG. 1.

However, since this psychotheraphy apparatus is operated in such a manner that the patient presses down buttons based on his/her own subjective determination to ultimately control the visual and auditory stimuli, there is a problem in that it is impossible to objectively confirm as to whether a desired emotion is properly induced based on the visual and auditory stimuli.

Further, U.S. Pat. No. 5,725,472 discloses a psychotheraphy apparatus wherein physiological responses of a patient and push-button responses of the patient to asked questions are monitored to cognize an emotion induction state and then visual, auditory, olfactory, and tactile stimuli are selectively controlled based on the cognized emotion induction state, thereby resulting in new emotional, psychological and cognitive response patterns in the patient, as shown in FIG. 2.

However, since this psychotheraphy apparatus is operated in such a manner that in order to ensure an accuracy of determination of emotion induction, the physiological responses of the patient is used only as auxiliary data for the determination of the emotion induction and the emotion induction state is cognized based on the button answers of the patient to the asked questions, there are problems in that it is difficult to objectively induce an emotion if the patient's responses are not clear, and that the patient's feelings cannot be naturally transmitted to the psychotheraphy apparatus since the patient should make an artificial effort to press down the buttons for expressing the patient's feelings. Moreover, the psychotheraphy apparatus has a limitation in that there is no specific suggestion regarding how to use the monitored physiological responses of the patient in the emotion induction.

SUMMARY OF THE INVENTION

The present invention is contemplated to solve the above problems. An object of the present invention is to provide an apparatus and method for inducing emotions, wherein biosignals from a user are fedback and it is objectively determined whether an emotion desired by the user is properly induced based on the fedback biosignals, so that the desired emotion can be accurately induced.

Another object of the present invention is to provide an apparatus and method for inducing emotions, wherein biosignals from a user are fedback and an emotion induction protocol capable of inducing a desired emotion is changed based on the fedback biosignals, thereby accelerating emotion induction.

According to one aspect of the present invention for achieving the above objects, there is provided an apparatus for inducing emotions based on detection of biosignals from a body of a user and on emotion induction protocols for selectively controlling visual, auditory, olfactory and tactile stimuli, comprising an emotion induction module for selecting an emotion induction protocol capable of inducing a desired emotion selected by the user, extracting one or more bioparameters from the biosignals, and changing the emotion induction protocol depending on increase/decrease patterns of the respective extracted bioparameters so as to induce the emotion; a biostimulation module for outputting physical signals for applying the stimuli to the user' body based on the selected emotion induction protocol; and a biosignal measurement module for detecting one or more biosignals from the user' body and outputting them to the emotion induction module before and after the output of the physical signals from the biostimulation module.

Further, according to another aspect of the present invention, there is provided a method for inducing emotions based on emotion induction protocols capable of selectively controlling visual, auditory, olfactory and tactile stimuli, comprising the steps of selecting a desired emotion by a user; detecting one or more biosignals from the user's body and extracting one or more bioparameters from the detected biosignals; outputting physical signals for stimulating the use's body based on an emotion induction protocol capable of inducing the selected emotion; after the output of the physical signals, detecting one or more biosignals from the user's body and extracting one or more bioparameters from the detected biosignals; and inducing the emotion by changing the emotion induction protocol based on increase/decrease patterns of the bioparameters extracted from the biosignals.

BRIEF DESCRIPTION OF THE DRAWINGS

The above and other objects, advantages and features of the present invention will become apparent from the following description of preferred embodiments given in conjunction with the accompanying drawings, in which:

FIG. 5 is a view showing an example of illumination, fragrance and contents for inducing emotions such as pleasure, sadness, anger, fear, disgust, and surprise;

FIGS. 6a to 6f are views showing examples of emotion induction protocols for inducing the emotions such as pleasure, sadness, anger, fear, disgust, and surprise;

FIG. 7 is a view showing an example of bioparameter change models;

FIG. 8 is a view showing deviations D ($d_0$, $d_1$, $d_2$) obtained by comparing increase/decrease patterns of the bioparameter change models with increase/decrease patterns of extracted respective bioparameters; and FIG. 9 is a view showing priorities of changes in the bioparameters for emotions including pleasure, sadness, anger, fear, disgust, and surprise.

DETAILED DESCRIPTION OF THE INVENTION

Hereinafter, an apparatus and method for inducing emotions according to the present invention will be explained in detail with reference to the accompanying drawings.

Figure 1:
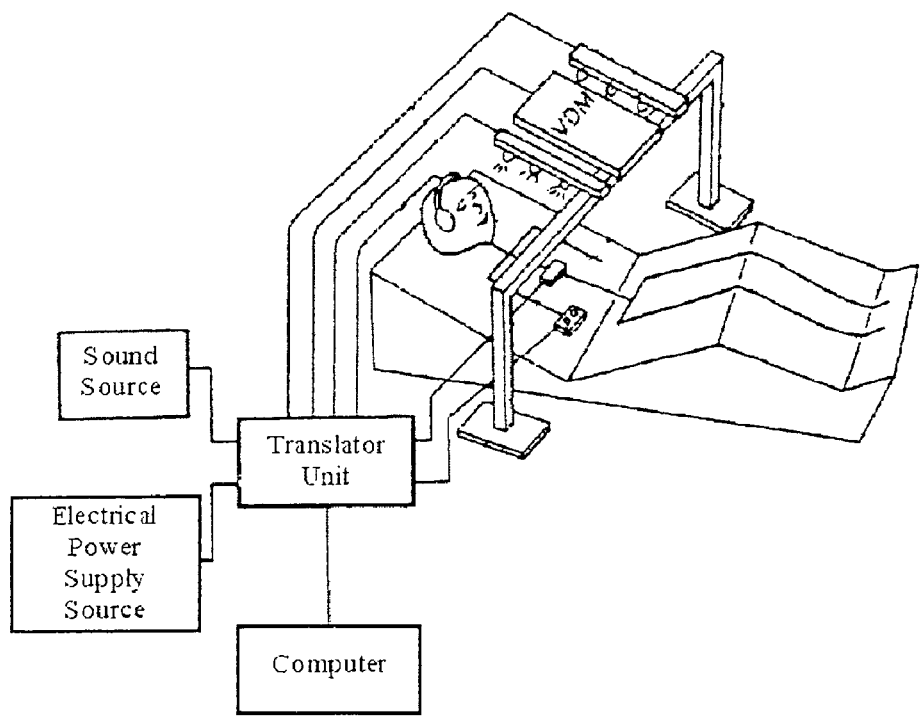
FIG. 1 is a view illustrating a method for confirming emotion induction in a conventional psychotheraphy apparatus.
Figure 2:
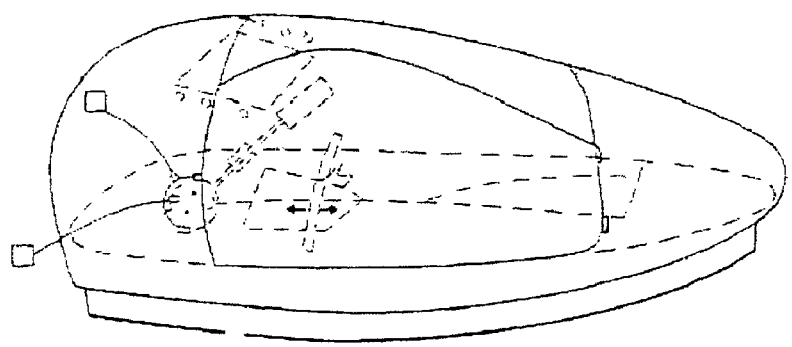
FIG. 2 is a view illustrating a method for confirming feeling induction in another conventional psychotheraphy apparatus.
Figure 3:
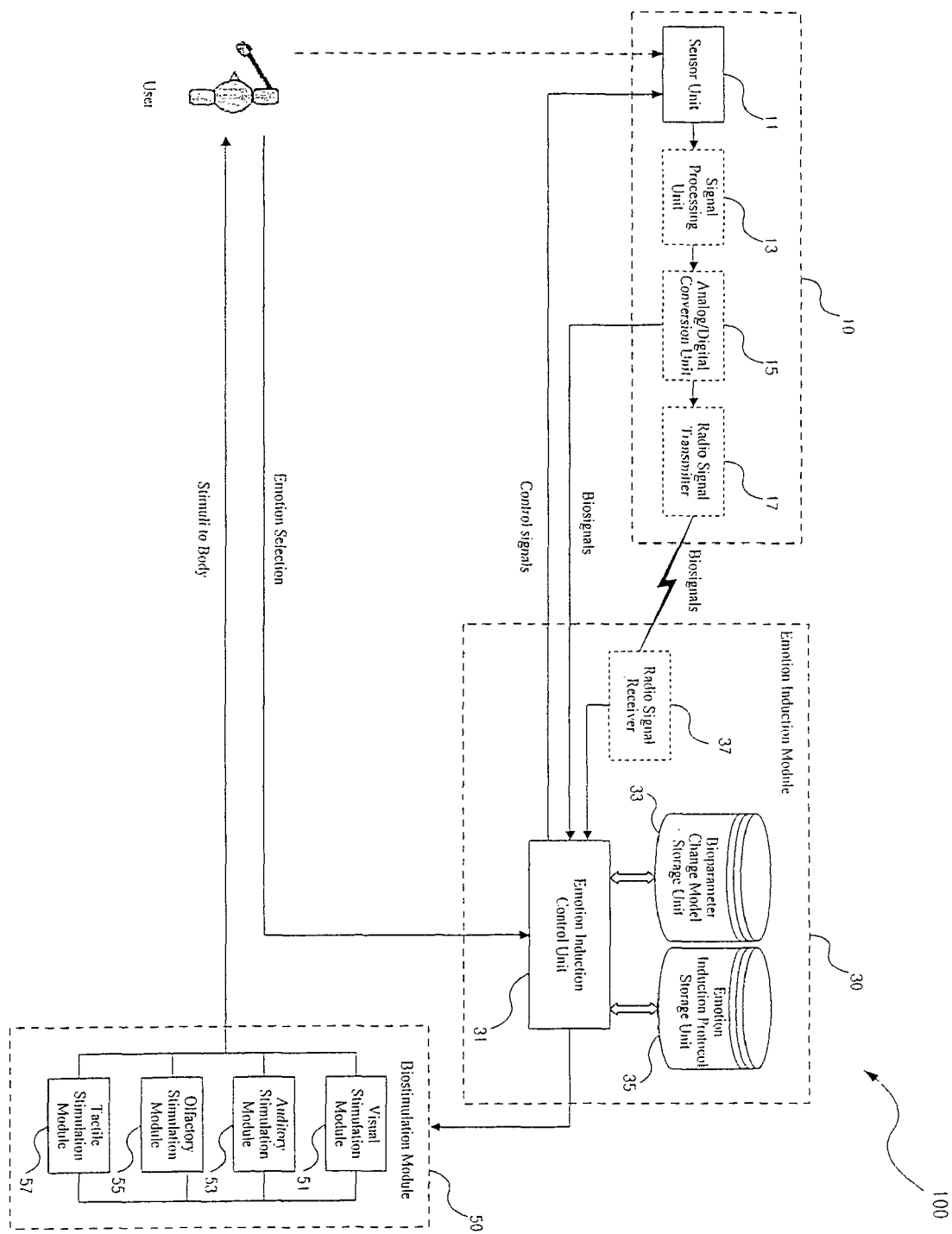
FIG. 3 is a schematic block diagram of an apparatus for inducing emotions according to the present invention.

FIG. 3 is a schematic block diagram of an apparatus for inducing emotions 100 according to the present invention. The apparatus 100 comprises a biosignal measurement module 10 for detecting biosignals from a body of a user, an emotion induction module 30 for inducing an emotion desired by the user, and a biostimulation module 50 for outputting physical signals for giving stimuli to the user's body.

Figure 4:
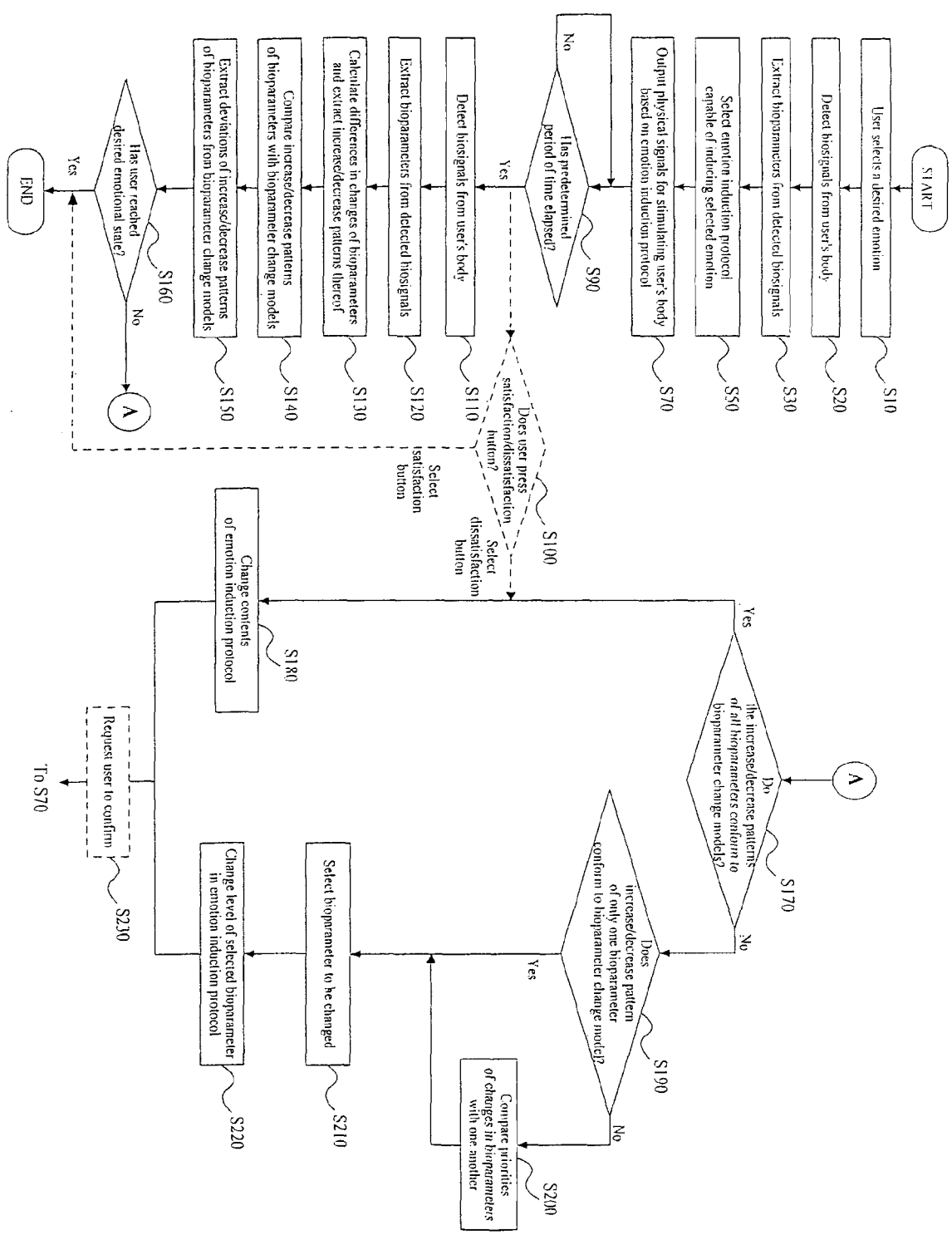
FIG. 4 is a flowchart illustrating entire procedures of a method for inducing emotions according to the present invention.

FIG. 4 is a flowchart illustrating a method for inducing an emotion according to the present invention. The method comprises the steps of, if the user selects an emotion, outputting the physical signals according to an emotion induction protocol for inducing the selected emotion (S10~S70), and changing the contents and level of the emotion induction protocol depending on increase/decrease patterns of the bioparameters before and after the output of the physical signals (S90~S220).

If the user first selects a desired emotion (S10), an emotion induction control unit 31 of the emotion induction module 30 outputs control signals corresponding to the selected emotion to the biosignal measurement module 10. The biosignal measurement module 10 detects one or more biosignals from the user's body through a sensor unit 11 in response to the control signals outputted from the emotion induction control unit 31 and then outputs the detected biosignals to the emotion induction control unit 31 (S20).

The biosignals detected from the user's body through the sensor unit 11 include biosignals for heartbeat and skin resistance. To this end, the sensor unit 11 includes a heartbeat detection sensor for detecting the heartbeat of the user's body, and a skin resistance sensor for detecting skin resistance. At this time, the heartbeat detection sensor is preferably implemented by an electrocardiogram (ECG) sensor for measuring an active current resulting from stretch and contraction of the heart muscle through electrodes attached to some portions of the user's body, or a photo-electric pulse Photoplethysmography (PPG) sensor for measuring changes in the optically measured amount of blood flow resulting from changes in the diameters of blood vessels due to the user's heartbeat. The skin resistance sensor can be implemented by a galvanic skin response (GSR) sensor for measuring changes in skin conduction coefficient due to sweat excreted from the user's skin by using electrodes directly or indirectly attached to the skin and a comparator connected to the electrodes.

According to a preferred embodiment of the present invention, the biosignal measurement module 10 comprises a signal processing unit 13 for amplifying and filtering the biosignals detected by the sensor unit 11, and an analog/digital conversion unit 15 by which if the biosignals are in the form of analog signals, the analog biosignals are converted into digital signals.

Further, according to another preferred embodiment of the present invention, the biosignal measurement module 10 can transmit and receive the control signals and biosignals to and from the emotion induction module 30 in a wired or wireless manner. To this end, the biosignal measurement module 10 includes a radio signal transmitter 17 for converting the biosignals into radio signals and transmitting the radio signals to the emotion induction module 30, and the emotion induction module 30 includes a radio signal receiver 37 for converting the radio signals received from the biosignal measurement module 10 into the biosignals.

Moreover, according to a further preferred embodiment of the present invention, the biosignal measurement module 10 can be made in the form of a wristwatch to be put on the user's wrist or in the form of a belt to be detachably attached to a predetermined portion of the user's body.

Then, the emotion induction control unit 31 extracts one or more bioparameters representing characteristics of the user's body from one or more biosignals detected from the user's body through the biosignal measurement module 10 for a predetermined period of time (S30).

For example, the emotion induction control unit 31 can extract bioparameters representing heart rate (HR) and heart rate variability (HRV) from a biosignal having information on the user's heartbeat, and a bioparameter representing the skin resistance from a biosignal having information on the user's skin resistance. A method for extracting such bioparameters is disclosed in detail in Korean Patent Laid-Open Publication No. 2002-0018541 entitled "Apparatus and Method for Cognizing Bodily and Emotional State" which will be briefly explained below.

Bioparameters RR, HR, LF, HF, LF/HF and RSA can be extracted from the heartbeat biosignal measured by the heartbeat detection sensor. The bioparameters RR, RSA and HR are first calculated from data of the user's heartbeat. The heartbeat data are then analyzed to obtain the bioparameter HRV which in turn is analyzed through Fast Fourier Transforms (FFT) to obtain the bioparameter LF/HF.

Furthermore, it is possible to extract the bioparameter SCL (Skin conductance level) representing an average of the reciprocals of the skin resistance from the skin resistance biosignal measured by the skin resistance sensor. From a graph plotted by converting the values of the skin resistance into their reciprocals, the bioparameter N-SCR (number of skin conductive responses) representing the number of positive zero crossings, or bioparameter SCRM (skin conductive response magnitude) representing heights from the positive zero crossings to negative zero crossings is extracted.

In order to control the emotion induction, this embodiment employs the bioparameters HR and HRV extracted from the heartbeat biosignal measurable by the heartbeat detection sensor, and the bioparameter SCRM extracted from the skin resistance biosignal measurable by the skin resistance sensor, among bioparameters that are remarkably changed depending on changes in the user's feelings.

Next, the emotion induction control unit 31 selects an emotion induction protocol capable of inducing an emotion which has been selected by the user from an emotion induction protocol storage unit 35 (S50). Hereinafter, the emotion induction protocol will be explained in more detail with reference to FIGS. 5 and 6.

FIG. 5 is a view showing an example of illumination, fragrance and contents for inducing emotions such as pleasure, sadness, anger, fear, disgust, and surprise. As shown in FIG. 5, it is known that yellow- or orange-based illumination induces pleasure and blue- or gray-based illumination induces sadness; grapefruit- or jasmine-based fragrance induces pleasure and juniper or bergamot fragrance induces sadness; and the contents of a cheer or a wedding ceremony induce pleasure while the contents of the death of one's parents or parting induce sadness.

The emotion induction protocol induces physiological signals for an emotional state by using mental effects on such visual, auditory, olfactory and tactile senses. Examples of emotion induction protocols for inducing emotions such as pleasure, sadness, anger, fear, disgust, and surprise are shown in FIGS. 6a to 6f.

As shown in FIGS. 6a to 6f, the emotion induction protocols are protocols configured by properly combining the contents and conditions of illumination, fragrance and temperature/humidity capable of inducing desired emotions. The contents and conditions of illumination, fragrance and temperature/humidity are graded according to the respective bioparameters into various levels in order of capability to induce the increase of the bioparameters.

Further, since the emotion induction protocol includes contents capable of inducing cognitive action by the central nervous system, and the conditions of illumination, fragrance and temperature/humidity capable of inducing physiological action of the autonomic nervous system, both the central and autonomic nervous systems of the user's body are stimulated according to the emotion induction protocol so that emotions can be efficiently induced.

Meanwhile, an initial level value of the emotion induction protocol is set to 0 in step 50. Although the contents of the emotion induction protocol are basically selected by the emotion induction control unit 31, the user may also select the contents by himself. It is preferred that the emotion induction protocol include a variety of contents according to the respective emotions so as to satisfy users' tastes.

Then, the biostimulation module 50 outputs the physical signals for stimulating visual, auditory, olfactory and tactile senses of the user's body according to the contents and level of the emotion induction protocol, which has been selected by the emotion induction control unit 31, through a visual stimulation module 51, an auditory stimulation module 53, an olfactory stimulation module 55 and a tactile stimulation module 57, for example, by displaying the contents of a wedding ceremony through a video device, turning on/off the power switch of an illuminator, or controlling fragrance injection (S70).

After a predetermined period of time has elapsed once the physical signals are outputted through the biostimulation module 50, the emotion induction control unit 30 outputs the control signals back to the biosignal measurement module 10 in order to confirm as to whether a desired emotion has been properly induced according to the stimulus applied to the user's body, and the biosignal measurement module 10 detects the biosignals for heartbeat and skin resistance in response to the control signals (S90 to S110). The emotion induction control unit 31 extracts the bioparameters HR, SCRM and HRV from the biosignals detected by the biosignal measurement module 10 (S120). At this time, the values of the respective bioparameters extracted in step 120 are values that have varied according to changes in the user's feelings due to the stimulus applied to the body.

Then, the emotion induction control unit 31 calculates differences between changes in the respective bioparameters before and after the output of the physical signals for stimulating the body and extracts the increase/decrease patterns of the respective bioparameters based on the calculated results (S130).

In order to check whether the user has reached a desired emotional state, the emotion induction control unit 31 subsequently compares the resulting increase/decrease patterns of the respective bioparameters with bioparameter change models stored in a bioparameter change model storage unit 33 and extracts deviations D ($d_0$, $d_1$, $d_2$) of the increase/decrease patterns of the respective bioparameters from the bioparameter change models (S140 and S150). Hereinafter, a method for extracting the deviations of the increase/decrease patterns of the respective bioparameters will be described in detail with reference to FIGS. 7 and 8.

FIG. 7 is a view showing an example of the bioparameter change models. An arrow ⇧ indicates the increase of the bioparameter, another arrow ⇩ indicates the decrease of the bioparameter, and arrows ↑ and ↓ indicate that the bioparameter is greatly increased and decreased, respectively. Here, "–" means that there is little or no change in the bioparameter.

As shown in FIG. 7, the bioparameters HR, SCRM and HRV represents respective particular changes in the respective emotional states. The bioparameter change models are obtained by modeling the increase/decrease patterns of the bioparameters acquired through many experiments on a large number of people in accordance with the respective emotions. In other words, the bioparameter change models are models for responses of the autonomic nervous system (ANS) in the emotional state such as pleasure, sadness, anger, fear, disgust and surprise, i.e. the increase/decrease patterns of the bioparameters HR, SCRM and HRV.

For instance, HR decreases and SCRM and HRV increase in an emotional state of pleasure; HR decreases and SCRM increases in an emotional state of sadness; and HR and SCRM increase and HRV decreases in an emotional state of anger.

This embodiment limits the bioparameters for use in the emotion induction to HR, SCRM and HRV and accordingly configures the bioparameter change models for the three bioparameters HR, SCRM and HRV as shown in FIG. 7. However, the aforementioned bioparameters such as SCL, SCR, RR and RSA may also be used for the emotion induction. In such a case, the bioparameter change models can be properly modified according to increase/decrease patterns of the bioparameters SCL, SCR, RR and RSA obtained through the experiments, as shown in Table 1 below.

TABLE 1

| Total | SCL | SCR | SCRM | RR | HR | RSA | HRV |
|---|---|---|---|---|---|---|---|
| Pleasure | — | ⇑ | ↑ | ⇑ | ⇓ | ⇑ | ⇑ |
| Sadness | — | ⇑ | ⇑ | ⇑ | ⇓ | ⇑ | — |
| Anger | ↑ | ↑ | ↑ | ↓ | ↑ | ⇓ | ⇓ |
| Fear | ⇑ | ↑ | ↑ | ⇑ | ⇓ | ⇑ | ⇑ |
| Disgust | ⇑ | ↑ | ⇑ | ↑ | ↓ | ⇑ | ⇑ |
| Surprise | — | ↑ | ↑ | ↑ | ↓ | ⇑ | ↑ |

FIG. 8 is a view showing the deviations D ($d_0$, $d_1$, $d_2$) obtained by comparing the increase/decrease patterns of the bioparameter change models with the increase/decrease patterns of the extracted respective bioparameters, where the deviations $d_0$, $d_1$ and $d_2$ of the increase/decrease patterns of the bioparameters HR, SCRM and HRV are expressed as numbers.

As shown in FIG. 8, the emotion induction control unit 31 compares the increase/decrease patterns of the respective bioparameters with the bioparameter change models and extracts the deviations D ($d_0$, $d_1$, $d_2$) of the increase/decrease patterns of the respective bioparameters based on comparative results. At this time, the deviations $d_0$, $d_1$, $d_2$ are set to 0 if the increase/decrease patterns of the extracted bioparameters are identical with the increase/decrease patterns of the bioparameter change models; 1 if the increase/decrease patterns of the extracted bioparameters are in a state reduced from the increase/decrease patterns of the bioparameter change models; and −1 if the increase/decrease patterns of the extracted bioparameters are in a state increased from the increase/decrease patterns of the bioparameter change models.

For example, if the increase/decrease patterns of HR, SCRM and HRV in the bioparameter change models are ⇑, ⇓ and ⇑, respectively, and the increase/decrease patterns of HR, SCRM and HRV extracted from the biosignal measurement module 10 are ⇑, ⇑ and ⇓, respectively, the deviation D=(0, −1, 1).

Meanwhile, although the deviations $d_0$, $d_1$, and $d_2$ of the increase/decrease patterns of the respective bioparameters are expressed as three numbers of −1, 0 and 1 in this embodiment, the expression of the deviations may be arbitrarily changed, for example, in such a manner that numbers are sequentially assigned thereto from 0 or special symbols are used therefor.

Then, the emotion induction control unit 31 checks whether the user has reached the desired emotional state based on the deviations D ($d_0$, $d_1$, $d_2$) of the increase/decrease patterns of the respective bioparameters (S160). If all the values of $d_0$, $d_1$ and $d_2$ are 0, this means that all the bioparameters are increased and decreased in the same way as the bioparameter change models. Thus, it is determined that the user has reached the desired emotional state. If not, it is determined that the user has not reached the desired emotional state.

In the meantime, it is also possible for the user to determine whether he/she has reached the desired emotional state, based on his/her own opinion in addition to the increase/decrease patterns of the extracted bioparameters (S100). In this case, the emotion induction control unit 31 recognizes that the user has reached the desired emotional state when the user presses a satisfaction button, and then, terminates the emotion induction process. If the user presses a dissatisfaction button, the emotion induction control unit 31 causes the user to select the other contents in the emotion induction protocol.

If the user has reached the desired emotional state, the emotion induction control unit 31 checks whether the increase/decrease patterns of all the bioparameters do not conform to the bioparameter change models (S170). If all the values of $d_0$, $d_1$, and $d_2$ are not 0, this means that all the bioparameters are increased and decreased differently from the bioparameter change models. Thus, the emotion induction control unit 31 changes the contents of the emotion induction protocol (S180). Here, the reason that the contents of the emotion induction protocol is caused to be changed is that the disagreement between the increase/decrease patterns of all the bioparameters and the bioparameter change models means that the current contents of the emotion induction protocol are inappropriate for the emotion induction since the user's cognition of the contents through cognitive action of his/her brains results in a change of the user's emotional state and thence changes in the values of the respective bioparameters.

Then, the biostimulation module 50 outputs the physical signals for applying the visual, auditory, olfactory and tactile stimuli to the user's body, based on the emotion induction protocol in which the contents thereof have been changed.

Meanwhile, if there is a bioparameter of which the increase/decrease pattern conforms to the bioparameter change model in step S170, it is checked whether an increase/decrease pattern of only one bioparameter does not conform to the bioparameter change model (S190). If two of the values of $d_0$, $d_1$, and $d_2$ are 0, this means that only one bioparameter is increased and decreased differently from the bioparameter change model. Thus, the bioparameter is selected as a bioparameter to be changed and then the level of the selected bioparameter in the emotion induction protocol is increased or decreased by one grade (S210 and S220).

Here, if the value of the deviation $d_0$, $d_1$, or $d_2$ of the increase/decrease pattern of the selected bioparameter is 1, this means that the increase/decrease pattern of the bioparameter is in a decreased state as compared with the increase/decrease pattern of the bioparameter change model. Thus, in order to cause the bioparameter to have the same increase/decrease pattern as the bioparameter change model, the value of the bioparameter should be increased. Accordingly, the level of the bioparameter in the emotion induction protocol is increased by one grade. Furthermore, if the value of the deviation $d_0$, $d_1$ or $d_2$ of the increase/decrease pattern of the selected bioparameter is −1, this means that the increase/decrease pattern of the bioparameter is in an increased state as compared with the increase/decrease pattern of the bioparameter change model. Thus, in order to cause the bioparameter to have the same increase/decrease pattern as the bioparameter change model, the value of the bioparameter should be decreased. Accordingly, the level of the bioparameter in the emotion induction protocol is decreased by one grade.

If the increase/decrease patterns of a plurality of bioparameters do not conform to those of the bioparameter change models in step S190 (only one of the values of $d_0$, $d_1$, and $d_2$ is 0), the priorities of changes in the bioparameters are compared with one another in accordance with the priorities of changes shown in FIG. 9 (S200). After a bioparameter more suitable for the emotion induction among the plurality of bioparameters is selected as a bioparameter to be changed (S210), the level of the selected bioparameter in the emotion induction protocol is increased or decreased by one grade (S220). At this time, the priorities of changes in the bioparameters are set in order of induction facilitation of the bioparameters for a relevant emotion induction.

Then, the biostimulation module 50 outputs the physical signals for applying the visual, auditory, olfactory and tactile stimuli to the user's body, based on the emotion induction protocol in which the level has been increased or decreased.

Meanwhile, it is preferred that when the contents of the emotion induction protocol are caused to be changed in step 180, the kind of the changed contents be temporarily stored. In such a case, it is possible to prevent identical contents from being selected when the contents may be changed again next time.

Likewise, it is preferred that when the level of the bioparameter in the emotion induction protocol in step 220 is increased or decreased by one grade, the kind and level value of the bioparameter be temporarily stored. In such a case, if the same bioparameter should be controlled next time, the emotion induction can be accelerated by increasing or decreasing the level of the bioparameter in the emotion induction protocol beyond or below the temporarily stored level value. For example, in a case where the level value of the SCRM in the emotion induction protocol is increased to 1, the bioparameter SCRM and its level value of 1 are temporarily stored. Then, if the level value of the SCRM should be increased again next time, the level value of the SCRM in the emotion induction protocol is increased to 2 with reference to the temporarily stored level value so that a stronger stimulus is outputted to the user's body, thereby accelerating the emotion induction.

Moreover, the process further comprises the step of informing the user of the application of the changed emotion induction protocol before the application thereof, i.e. before the physical signals for stimulating the user's body are outputted according to the changed emotion induction protocol (S230). Thus, it is possible to prevent the contents or level in the emotion induction protocol from being arbitrarily changed in a transient state where the user is about to be, for example, pleased or sad so that the emotion induction can be continuously performed.

For facilitating understanding of the present invention, a preferred embodiment of the present invention will be described in connection with a case where the user selects an emotion of anger.

First, in the emotion induction protocol capable of inducing anger (see FIG. 6c), a protocol having a level value of 0, i.e. a protocol in which the illumination is set to red, the fragrance is set to peppermint, the temperature is set to 26° C., and the humidity is set to 70%, is selected.

Assuming that the contents of rape capable of inducing anger are selected, physical signals for displaying the contents of rape onto a screen, irradiating the red illumination, injecting the peppermint fragrance, and controlling the temperature and humidity are outputted through the biostimulation module 50.

Then, the emotion induction control unit 31 calculates differences in changes of the bioparameters before and after the output of the physical signals for stimulating the user's body, extracts the increase/decrease patterns of the respective bioparameters, compares the increase/decrease patterns with the bioparameter change models, and extracts the deviations D ($d_0$, $d_1$, $d_2$) of the increase/decrease patterns of the respective bioparameters from the bioparameter change models.

For example, in a case where the bioparameter HR is increased, SCRM is reduced, and HRV is increased, the emotion induction control unit 31 compares the increase/decrease patterns of the bioparameters HR, SCRM and HRV with the bioparameter change models and then extracts the deviations $d_0=0$, $d_1=1$ and $d_2=-1$ of the increase/decrease patterns of the bioparameters HR, SCRM and HRV from the bioparameter change models.

Then, since the deviation D of the increase/decrease patterns of the respective bioparameters is (0, 1, −1), the emotion induction control unit 31 determines that the user has not yet reached the desired emotional state. Further, since the increase/decrease patterns of the two bioparameters SCRM and HRV do not conform to the bioparameter change models, the emotion induction control unit 31 sets the SCRM as a bioparameter to be changed in accordance with the priorities shown in FIG. 9, and then upgrades the level in the protocol for the SCRM shown in FIG. 6c by one grade and thus selects a protocol having a level value of 1, i.e. a protocol in which the illumination is set to pink, the fragrance is set to juniper, the temperature is set to 27° C., and the humidity is set to 75%.

Then, the physical signals for stimulating the visual, auditory, olfactory and tactile senses of the user's body are outputted through the biostimulation module 50 according to the selected emotion induction protocol. After stimulation of the user's body, biosignals from the user's body are fedback again and the above process is repeated until the desired emotion is induced.

As described above, according to the present invention, there is an advantage in that it is possible to objectively determine whether a desired emotion is properly induced based on the fedback biosignals from the user and thus the emotion desired by the user can be accurately induced.

Further, according to the present invention, there is another advantage in that the emotion induction protocol capable of inducing the desired emotion is changed depending on the fedback biosignals and thus the emotion induction can be accelerated as compared with the conventional apparatus for inducing the emotion.

Moreover, in a case where the present invention is applied to equipment such as mobile communications terminals and personal computers, it can be expected to obtain an effect of improving mental health through emotional purification since the user can properly control his/her own feelings all the time at any place.

Although the present invention has been described by way of example in connection with the preferred embodiment illustrated in the drawings, it will be understood by those skilled in the art that various changes and equivalent embodiments thereof may be made. In particular, although the inducible emotional state has been limited to the six emotional states of pleasure, sadness, anger, fear, disgust and surprise in the preferred embodiment, the method for inducing the emotion according to the present invention is not limited thereto. It is also possible to induce various emotional states by using the bioparameters RR, HR, RSA, HRV, HF, LF and LF/HF regarding the heartbeat measured by the heartbeat detection sensor and the bioparameters SCL, N-SCR and SCRM regarding the skin resistance measured by the skin resistance sensor. Therefore, the true technical scope of the present invention should be defined by the technical spirit of the appended claims.

What is claimed is:

1. An apparatus that induces emotions based on detection of measurable physiological biosignals from a body of a user and on emotion induction protocols that selectively control visual, auditory, olfactory and tactile stimuli, comprising:

an emotion induction device that selects from a plurality of emotion induction protocols stored in an electronic memory device an emotion induction protocol corresponding to a desired emotion selected by the user, extracts one or more electrical bioparameters from the physiological biosignals, and changes the emotion induction protocol depending on increase/decrease patterns of the respective extracted bioparameters so as to induce the emotion, wherein each emotion induction protocol corresponds to induce a different emotion and combines contents that induce cognitive action of the central nervous system and conditions that induce physiological action of the autonomic nervous system;
a biostimulation device that outputs physical signals that apply the stimuli to the user's body based on the selected emotion induction protocol; and
a biosignal measurement device that detects one or more biosignals from the user's body and outputs them to the emotion induction device before and after the output of the physical signals from the biostimulation device.

2. The apparatus as claimed in claim 1, wherein the emotion induction protocols correspond to at least two or more of the emotions of pleasure, sadness, anger, fear, disgust and surprise.

3. The apparatus as claimed in claim 1, wherein the emotion induction device comprises a bioparameter change model storage unit in which change models for the respective bioparameters by emotional states are stored, an emotion induction protocol storage unit in which the emotion induction protocols inducing physiological signals for the emotional states are stored, and an emotion induction control unit that compares the increase/decrease patterns of the respective bioparameters extracted from the biosignals with the bioparameter change models and changes the emotion induction protocols depending on comparison results.

4. The apparatus as claimed in claim 3, wherein the conditions that induce physiological action of the autonomic nervous system include illumination, fragrance and temperature/humidity.

5. The apparatus as claimed in claim 4, wherein each emotion induction protocol includes the contents and the conditions of illumination, fragrance and temperature/humidity being graded according to the respective bioparameters into various levels in order of a degree to which the contents and the conditions induce an increase pattern of the bioparameters.

6. The apparatus as claimed in claim 3, wherein the emotion induction control unit compares the increase/decrease patterns of the respective bioparameters extracted from the biosignals with the bioparameter change models, extracts deviations of the increase/decrease patterns of the respective bioparameters from the bioparameter change models, and checks whether the user has reached the desired emotional state based on the deviations of the increase/decrease patterns of the respective bioparameters.

7. The apparatus as claimed in claim 3, wherein if an increase/decrease pattern of only one bioparameter among the bioparameters extracted from the biosignals does not conform to the bioparameter change model, the emotion induction control unit changes a level of the non-conforming bioparameter in the emotion induction protocol.

8. The apparatus as claimed in claim 3, wherein if increase/decrease patterns of a plurality of bioparameters among the bioparameters extracted from the biosignals do not conform to the bioparameter change models, the emotion induction control unit changes levels of bioparameters, which are selected according to priorities of changes in the bioparameters, in the emotion induction protocol.

9. The apparatus as claimed in claim 8, wherein the priorities of changes in the bioparameters are set in order of induction facilitation of the bioparameters for a relevant emotion induction.

10. The apparatus as claimed in claim 3, wherein if increase/decrease patterns of all the bioparameters extracted from the biosignals do not conform to the bioparameter change models, the emotion induction control unit changes the contents of the emotion induction protocol.

11. The apparatus as claimed in claim 1, wherein the physical signals outputted from the biostimulation device stimulate at least one of the visual, auditory, olfactory and tactile senses.

12. The apparatus as claimed in claim 1, wherein the biosignal measurement device comprises a sensor unit that detects one or more biosignals from the user's body, and the sensor unit includes a heartbeat detection sensor that detects a heartbeat biosignal from the user's body and a skin resistance sensor that measures skin resistance of the user's body.

13. The apparatus as claimed in claim 12, wherein bioparameters for the number of heartbeats and a variation of the heartbeat are extracted from the heartbeat biosignal, and a bioparameter for the skin resistance is extracted from a skin resistance biosignal.

14. The apparatus as claimed in claim 1, wherein the biosignal measurement device further comprises a signal processing unit that amplifies and filters the detected biosignals, an analog/digital conversion unit that converts the detected biosignals into digital signals if the detected biosignals are in the form of analog signals, and a radio signal transmitter that converts the digital biosignals outputted from the analog/digital conversion unit into radio signals and transmits the radio signals.

15. A method for inducing emotions based on emotion induction protocols that selectively control visual, auditory, olfactory and tactile stimuli, comprising the steps of:
selecting from a plurality of emotion induction protocols stored in an electronic memory device an emotion induction protocol corresponding to a desired emotion selected by a user, wherein each emotion induction protocol corresponds to a different emotion and combines contents that induce cognitive action of the central nervous system and conditions that induce physiological action of the autonomic nervous system;
electronically converting one or more measurable physiological biosignals from the user's body and extracting one or more electrical bioparameters from the biosignals;
outputting physical signals that physically stimulate the user's body based on the electronically selected emotion induction protocol configured corresponding to the selected emotion;
after outputting the physical signals, electronically converting one or more physiological measurable biosignals from the user's body and extracting one or more electrical bioparameters from the biosignals; and
inducing the emotion by changing the emotion induction protocol based on increase/decrease patterns of the electrical bioparameters extracted from the biosignals.

16. The method as claimed in claim 15, wherein the emotion induction protocols correspond to at least two or more of the emotions of pleasure, sadness, anger, fear, disgust and surprise.

17. The method as claimed in claim 15, wherein the conditions that induce physiological action of the autonomic nervous system include illumination, fragrance and temperature/humidity.

18. The method as claimed in claim 17, wherein each emotion induction protocol includes the contents and the conditions of illumination, fragrance and temperature/humidity being graded according to the respective bioparameters into various levels in order of a degree to which the contents and the conditions induce an increase pattern of the bioparameters.

19. The method as claimed in claim 15, wherein the physical signals stimulate at least one of the visual, auditory, olfactory and tactile senses.

20. The method as claimed in claim 15, wherein the biosignals include biosignals for heartbeat and skin resistance of the user's body.

21. The method as claimed in claim 20, wherein bioparameters for the number of heartbeats and a variation of the heartbeat are extracted from the heartbeat biosignal, and a bioparameter for the skin resistance is extracted from the skin resistance biosignal.

22. The method as claimed in claim 15, wherein the detected biosignals are amplified and filtered; if the detected biosignals are in the form of analog signals, the step of detecting further comprises the steps of converting the analog biosignals into digital biosignals; and converting the digital biosignals into radio signals and transmitting the radio signals.

23. The method as claimed in claim 15, wherein the step of inducing the emotion further comprises the steps of comparing the increase/decrease patterns of the extracted respective bioparameters with the respective bioparameter change models, extracting deviations of the increase/decrease patterns of the respective bioparameters from the bioparameter change models, and checking whether the user has reached a desired emotional state based on the deviations of the increase/decrease patterns of the respective bioparameters.

24. The method as claimed in claim 18, further comprising the step of, if the user has not reached a desired emotional state, changing the contents or level of the emotion induction protocol.

25. The method as claimed in claim 24, wherein the step of changing the contents or level of the emotion induction protocol comprises the step of, if an increase/decrease pattern of only one bioparameter among the bioparameters extracted from the biosignals does not conform to the bioparameter change model, changing the level of the non-conforming bioparameter in the emotion induction protocol.

26. The method as claimed in claim 24, wherein the step of changing the contents or level of the emotion induction protocol comprises the step of, if increase/decrease patterns of a plurality of bioparameters among the bioparameters extracted from the biosignals do not conform to the bioparameter change models, changing the levels of bioparameters, which are selected according to priorities of changes in the bioparameters, in the emotion induction protocol.

27. The method as claimed in claim 26, wherein the priorities of changes in the bioparameters are set in order of induction facilitation of the bioparameters for a relevant emotion induction.

28. The method as claimed in claim 24, wherein the step of changing the contents or level of the emotion induction protocol comprises the step of, if increase/decrease patterns of all the extracted bioparameters do not conform to the bioparameter change models, changing the contents of the emotion induction protocol.

29. The apparatus as claimed in claim 5, wherein if an increase/decrease pattern of only one bioparameter among the bioparameters extracted from the biosignals does not conform to the bioparameter change model, the emotion induction control unit changes the level of the non-conforming bioparameter in the emotion induction protocol.

30. The apparatus as claimed in claim 5, wherein if increase/decrease patterns of a plurality of bioparameters among the bioparameters extracted from the biosignals do not conform to the bioparameter change models, the emotion induction control unit changes the levels of bioparameters, which are selected according to priorities of changes in the bioparameters, in the emotion induction protocol.

31. The apparatus as claimed in claim 5, wherein if increase/decrease patterns of all the bioparameters extracted from the biosignals do not conform to the bioparameter change models, the emotion induction control unit changes the contents of the emotion induction protocol.

32. The method as claimed in claim 23, further comprising the step of, if the user has not reached a desired emotional state, changing the contents or level of the emotion induction protocol.

33. An apparatus that induces emotions based on receiving measurable physiological biosignals from a body of a user and on emotion induction protocols that selectively control visual, auditory, olfactory and tactile stimuli, comprising:
an emotion induction device that receives a selection for a desired emotion by a user and selects from a plurality of emotion induction protocols stored in an electronic memory device an emotion induction protocol configured corresponding to the desired emotion, extracts one or more electrical bioparameters from respective physiological biosignal data of the biosignals, and changes the emotion induction protocol depending on increase/decrease patterns of the respective extracted bioparameters so as to induce the desired emotion, wherein each emotion induction protocol corresponds to a different emotion and combines contents that induce cognitive action of the central nervous system and conditions that induce physiological action of the autonomic nervous system;
a biostimulation device that outputs physical signals to the user to physically stimulate the user's body with the desired emotion based on the selected emotion induction protocol; and
a biosignal measurement device that receives one or more biosignals from the user's body and outputs them to the emotion induction device before and after the output of the physical signals from the biostimulation device.

34. A method for inducing emotions based on emotion induction protocols that selectively control visual, auditory, olfactory and tactile stimuli, comprising the steps of:
receiving a selection for a desired emotion by a user and selecting from a plurality of emotion induction protocols stored in an electronic memory device an emotion induction protocol corresponding to the desired emotion, wherein each emotion induction protocol corresponds to induce a different emotion and combines contents that induce cognitive action of the central nervous system and conditions that induce physiological action of the autonomic nervous system;
receiving one or more measurable physiological biosignals from the user's body to obtain respective biosignal data, and extracting one or more electrical bioparameters from the respective biosignal data;
outputting physical signals to the user to physically stimulate the user's body based on the electronically selected emotion induction protocol corresponding to the selected emotion;
after outputting the physical signals, receiving one or more measurable physiological biosignals from the user's body to obtain respective biosignal data, and extracting one or more electrical bioparameters from the respective biosignal data; and
inducing the emotion by changing the emotion induction protocol based on increase/decrease patterns of the electrical bioparameters extracted from the biosignal data, wherein physical signals are outputted to the user to physically stimulate the user's body with the desired emotion based on the changed emotion induction protocol.

* * * * *

UNITED STATES PATENT AND TRADEMARK OFFICE
CERTIFICATE OF CORRECTION

PATENT NO. : 7,955,259 B2  
APPLICATION NO. : 10/603787  
DATED : June 7, 2011  
INVENTOR(S) : Mihee Lee et al.

It is certified that error appears in the above-identified patent and that said Letters Patent is hereby corrected as shown below:

On the Title Page, Item (57) (Abstract), Line 5, Delete "feedback" and insert -- fedback --, therefor.

Signed and Sealed this
Fourteenth Day of February, 2012

David J. Kappos
*Director of the United States Patent and Trademark Office*